(12) United States Patent
Kato

(10) Patent No.: US 7,278,974 B2
(45) Date of Patent: Oct. 9, 2007

(54) MEDICAL GUIDE WIRE

(75) Inventor: Tomihisa Kato, Aichi-ken (JP)

(73) Assignee: Asahi In Tecc Co., Ltd., Nagoya (JP)

(*) Notice: Subject to any disclaimer, the term of this patent is extended or adjusted under 35 U.S.C. 154(b) by 217 days.

(21) Appl. No.: 10/919,476

(22) Filed: Aug. 17, 2004

(65) Prior Publication Data
US 2005/0203442 A1 Sep. 15, 2005

(30) Foreign Application Priority Data
Mar. 15, 2004 (JP) .............................. 2004-071846

(51) Int. Cl.
*A61B 5/00* (2006.01)
*A61M 25/00* (2006.01)

(52) U.S. Cl. ................................................ 600/585

(58) Field of Classification Search ................ 600/585, 600/433–435
See application file for complete search history.

(56) References Cited

U.S. PATENT DOCUMENTS

| | | |
|---|---|---|
| 4,721,117 A | 1/1988 | Mar et al. |
| 5,007,434 A * | 4/1991 | Doyle et al. ................ 600/585 |
| 5,253,653 A | 10/1993 | Daigle et al. |
| 5,259,393 A * | 11/1993 | Corso et al. ................ 600/585 |
| 5,606,981 A * | 3/1997 | Tartacower et al. ......... 600/585 |
| 5,666,969 A * | 9/1997 | Urick et al. ................ 600/585 |
| 6,612,998 B2 * | 9/2003 | Gosiengfiao et al. ....... 600/585 |
| 2004/0064069 A1 | 4/2004 | Reynolds et al. |

FOREIGN PATENT DOCUMENTS

| | | |
|---|---|---|
| EP | 1 266 670 A1 | 12/2002 |
| JP | 8-173547 | 7/1996 |
| JP | 2001-178829 | 7/2001 |

OTHER PUBLICATIONS

English Language Abstract of JP Publication No. 2001-178829; published Mar. 7, 2001.

* cited by examiner

*Primary Examiner*—Max F. Hindenburg
*Assistant Examiner*—Jonathan Foreman
(74) *Attorney, Agent, or Firm*—Morgan, Lewis & Bockius LLP

(57) ABSTRACT

In a medical guide wire, a front end of a core member is tapered off or diametrically reduced successively as it approaches a leading end tip to form a frustoconical configuration. A helical spring and the core member are spaced to form a non-integral zone extending at least 20 mm from a front end of the diameter-reduced front end portion. An inner circumference of the helical spring and an outer circumference of the core member are concentrically secured to form a plurality of securement points aligned in the lengthwise direction at regular spans so as to enable an operator to steer the guide wire with an improved rotation-following capability.

8 Claims, 5 Drawing Sheets

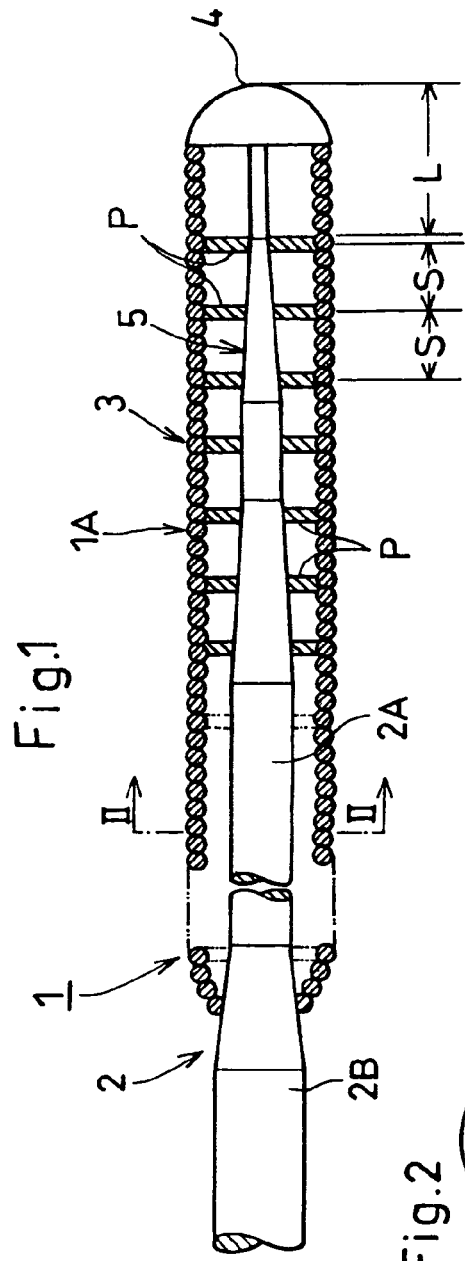
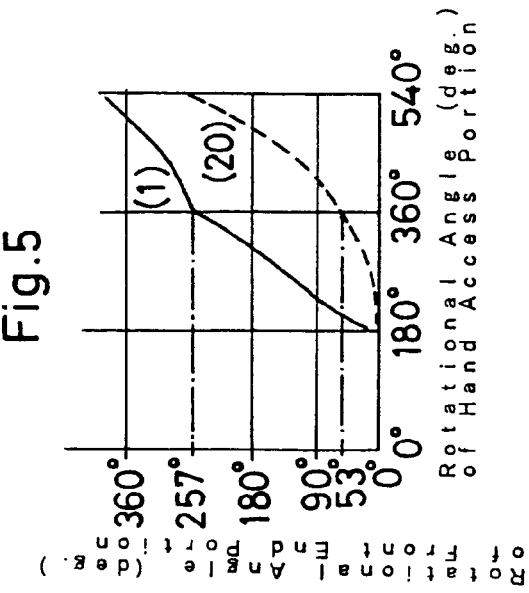
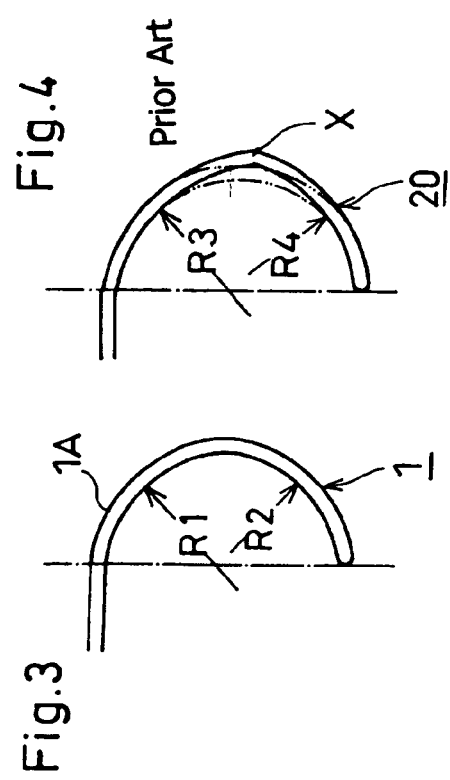

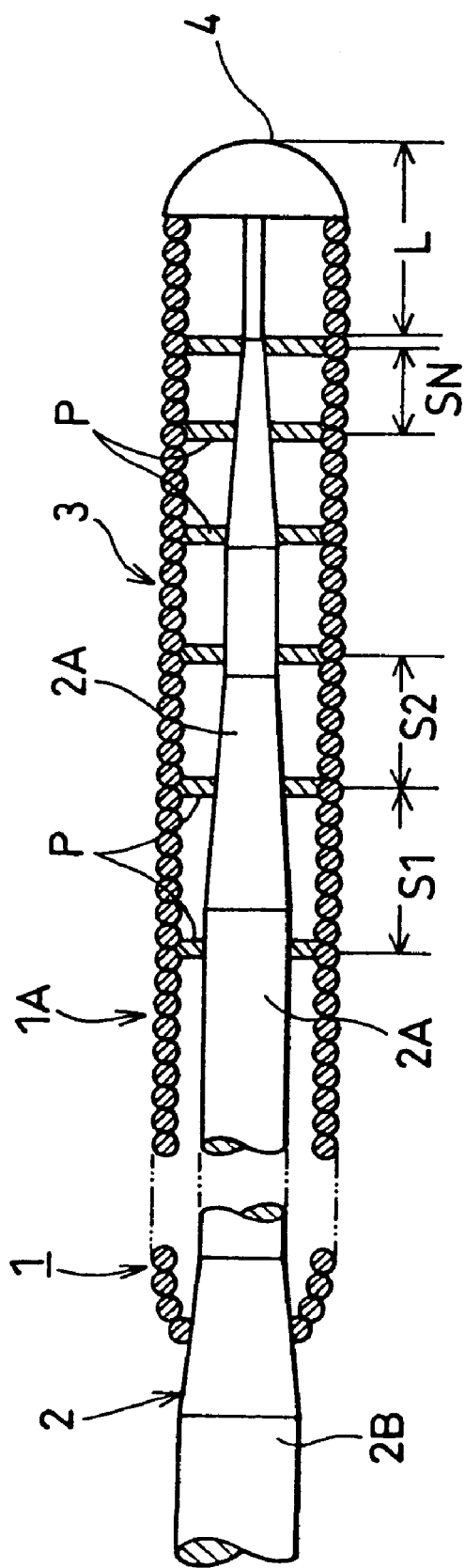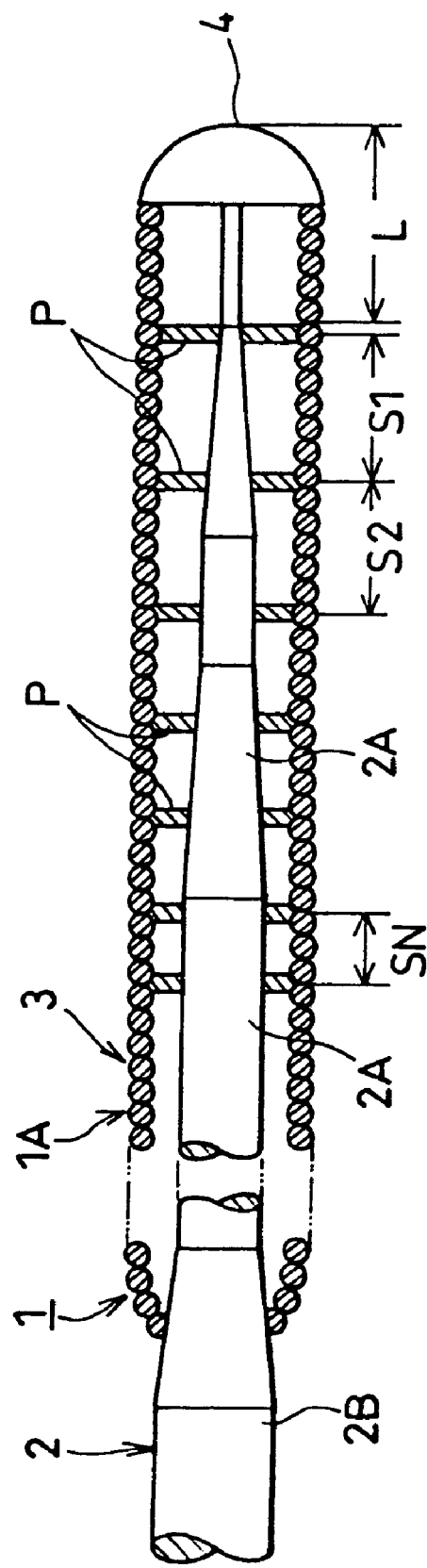

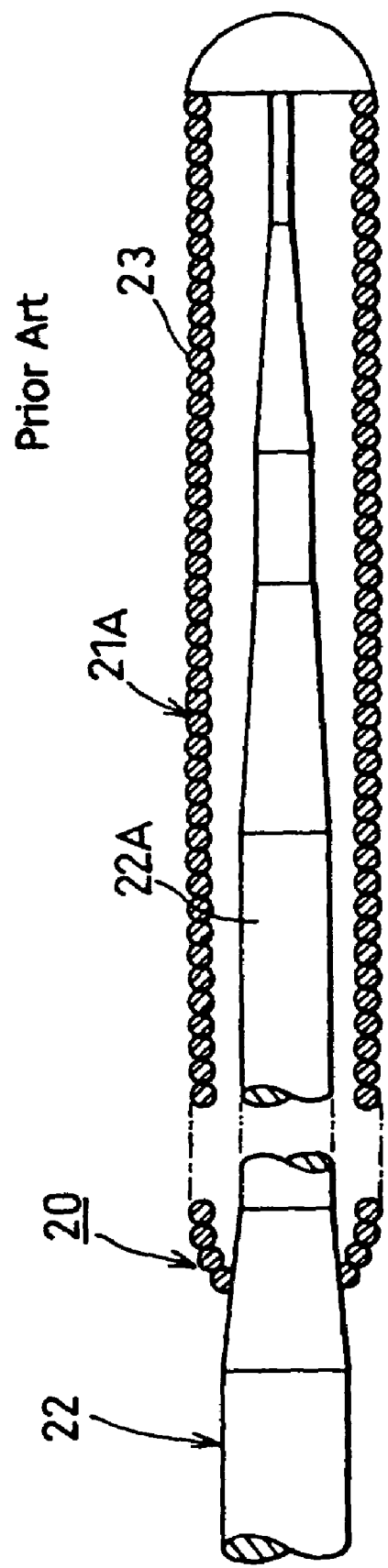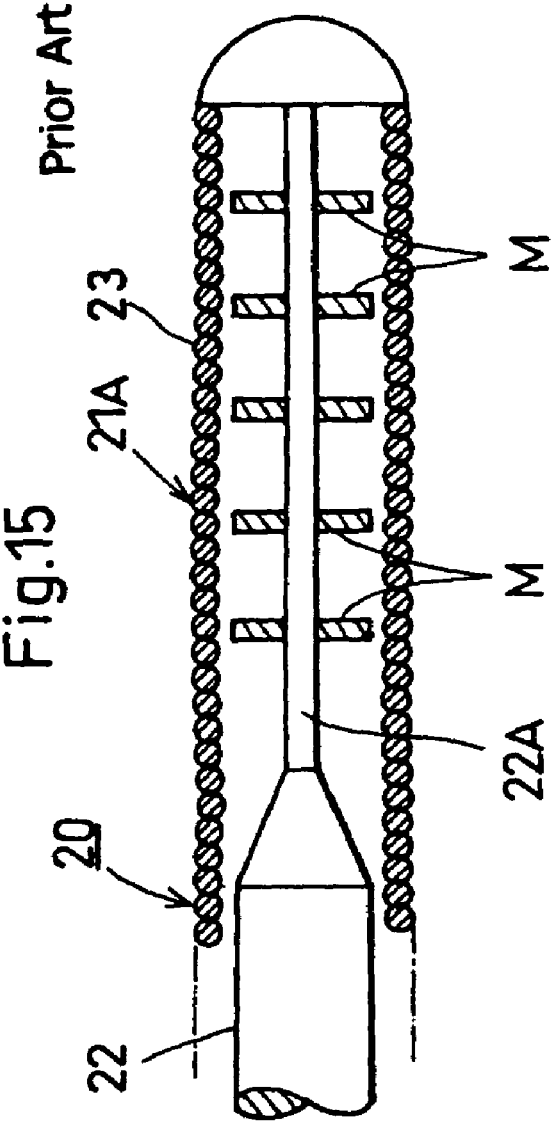

MEDICAL GUIDE WIRE

BACKGROUND OF THE INVENTION

1. Field of the Invention

The invention relates to a medical guide wire provided to assist a catheter when inserting it into a somatic cavity to cure or examine a diseased area (e.g., vascular stenosis area) and used to measure the diseased area.

2. Description of Related Art

In a medical guide wire which introduces a leading distal end into a diseased area through a sinuous vascular system, the leading distal end of the medical guide wire is inserted into the blood vessel or the somatic cavity by a "push-pull and turn" manipulation at a hand access portion located outside a subject patient upon treating the diseased area.

In order to achieve a smooth manipulation when inserting the leading distal end into the somatic cavity and the blood vessel, the medical guide wire requires multi-mechanical properties. The multi-mechanical properties are represented by a high flexibility, a good straightness and an improved restitutivity from a bending deformation. The medical guide wire of this type requires high flexibility at its leading distal end, while at the same time, appropriate rigidity is required at its rear portion. It is also indispensable for the leading distal end to have a high maneuverability in which the leading distal end properly responds to the hand operation which is to be done outside the subject patient.

As shown in FIG. 14, a medical guide wire 20 has basically an elongated and flexible front end portion 21A which has a diameter-increased hand access portion 22B and a tapered-off front end 22A of the core member 22. A helical spring 23 is secured to both ends of the tapered-off front end 22A.

With the basic structure of FIG. 14 in mind, Japanese Laid-open Patent Application No. 2001-178829 discloses a reverse blood stream stop means provided as an annular weir between an inner circumference of the helical spring 23 and the front end 22A of the core member 22 so as to prevent the reverse blood stream from entering into the helical spring 23 through gaps appeared between coil lines of the helical spring 23.

Japanese Laid-open Patent Application No. 8-173547 discloses a connection securement between an inner circumference of the helical spring 23 and an outer circumference of the front end 22A of the core member 22 so as to prevent the front end 22A from being inadvertently broken due to a stress concentration.

Japanese Domestic Laid-open Patent Application No. 7-500749 discloses radiopaque markers M as shown in FIG. 15. The radiopaque markers M are secured to an outer circumference of the tapered-off front end 22A with an annular space provided between the markers M and the helical spring 23. Alternatively, the markers M are secured to an inner circumference of the helical spring 23 with an annular space provided between the markers M and the front end 22A of the core member 22. The markers M enable a manipulator to measure the diseased area upon inserting the guide wire into the somatic cavity while projecting the radiation rays against the markers M.

The reverse blood stream stop means, the connection securement and the radiopaque markers M are placed within a space which is provided inside the helical spring 23. This negatively affects the bending characteristics upon inserting the front end portion 21A into a sinuous or tortuous path within the somatic cavity, or guiding the front end portion 21A selectively into one of the bifurcated portions of the blood vessel. This also negatively affects the steerability when implementing the "push-pull and turn" manipulation at the hand access portion located outside the subject patient upon treating the diseased area.

Therefore, it is an object of the invention to overcome the above drawbacks so as to provide a high quality medical guide wire which contributes to curing a diseased area with a good performance.

SUMMARY OF THE INVENTION

According to the present invention, there is provided a medical guide wire in which a flexible elongated core member has a diameter-reduced front end portion and a hand access portion diametrically greater than the diameter-reduced front end portion, and a helical spring is secured at both ends to the diameter-reduced front end portion.

The diameter-reduced front end portion is diametrically decreased progressively toward a front end of the diameter-reduced front end portion or is tapered-off toward the front end of said diameter-reduced front end portion. The helical spring and the core member are spaced to form a non-integral zone extending at least 20 mm from the front end of said diameter-reduced front end portion. An inner circumference of the helical spring and an outer circumference of the core member are secured to form a plurality of securement points aligned in the lengthwise direction at predetermined spans.

Namely, the medical guide wire according to the present invention, the core member and the helical spring secured to the core member are integrated into one piece via the securement points to provide a soft and flexible elongation structure. This structure imparts to the medical guide wire a good steerability with an improved bending characteristics.

According to another aspect of the present invention, the securement points are aligned in the lengthwise direction of the core member at series intervals.

According to another aspect of the present invention, the securement points are aligned at regular or irregular intervals in the lengthwise direction of the core member.

According to another aspect of the present invention, the helical spring is single wound configuration made from a single wire element.

According to another aspect of the present invention, the securement points are formed with a radiopaque material.

According to another aspect of the present invention, a front half of the helical spring is a radiopaque helical portion and a rear half of the helical spring is a radiotransparent helical portion, and the length of the radiopaque helical portion is an integral multiple of the span of the securement points, and the securement points are formed by a radiopaque material and placed on the radiotransparent helical portion.

According to another aspect of the present invention, a relationship of $SD/SA \leqq (D2/D1)^4$ is defined between first and second denominators and first and second numerators. Where, the first denominator is a dimension of the span SA between the securement points at the diameter-increased portion of the core member, the first numerator is a dimension of the span SB between the securement points at the diameter-reduced portion of the core member, the second denominator is a diametrical dimension D1 of the diameter-increased portion of the core member, and the second numerator is a diametrical dimension D2 of the diameter-reduced portion of the core member.

The non-integral zone extends at least 20 mm from the front end of the diameter-reduced front end portion. This is because a fingertip operation makes it possible to deform the front end portion of the medical guide wire into a dog-legged configuration to ensure a preshaping characteristic while securing a good flexibility smooth enough to insert the front end portion of the medical guide wire into the somatic cavity. The non-integral zone means an area in which the securement points are nonexistent. With the securement points concentrically provided between the helical spring and core member, it is possible to impart an improved rotation-following capability to the guide wire and navigate the guide wire with a good steerability.

It is preferable that the securement points make the front end align in a concentric relationship with the helical spring. However, considering the microstructure of the front end and the helical spring, the front end may be made aligned either in concentric or eccentric relationship with the helical spring.

BRIEF DESCRIPTION OF THE DRAWINGS

Preferred forms of the present invention is illustrated in the accompanying drawings in which:

FIG. 1 is a longitudinal cross sectional view of a medical guide wire according to a first embodiment of the invention;

FIG. 2 is a latitudinal cross sectional view taken along the line II-II of FIG. 1;

FIG. 3 is an explanatory view showing how a front end portion of the medical guide wire works;

FIG. 4 is an explanatory view showing how a front end portion of a prior art medical guide wire works;

FIG. 5 is a graphical representation of the mechanical characteristics of the medical guide wire;

FIGS. 6 and 7 are longitudinal cross sectional views of a medical guide wire according to a second embodiment of the invention;

FIGS. 14 and 15 are longitudinal cross sectional views of the prior art medical guide wire.

DETAILED DESCRIPTION OF THE PREFERRED EMBODIMENTS

Figure 8:
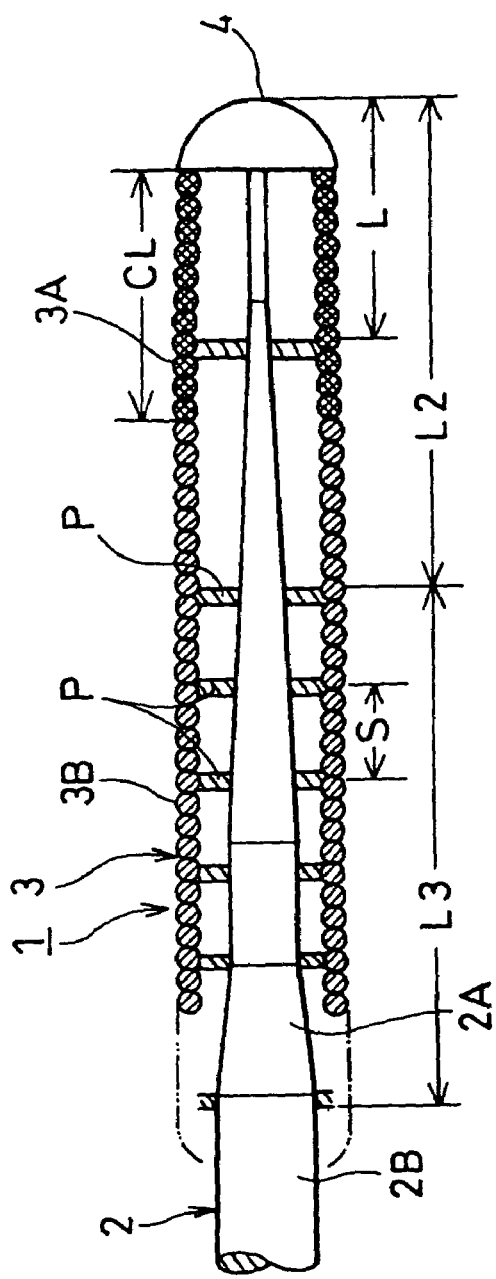
FIG. 8 is a longitudinal cross sectional view of a medical guide wire according to a third embodiment of the invention.

In the following description of the-depicted embodiments, the same reference numerals are used for features of the same type. Referring to FIGS. 1 through 5, a medical guide wire 1 (abbreviated as "guide wire 1" hereinafter) according to a first embodiment of the invention is described below.

An entire length of the guide wire 1 is approximately 1500 mm, and a front end portion 1A of the guide wire 1 is approximately 300 mm. A front end 2A of a flexible elongation core member 2 is diametrically decreased successively in a fashion tapered-off from a hand access portion 2B (approx. 0.193 mm in diameter) to a leading end tip 4 (approx. 0.03 mm in diameter) so as to generally form a frustocone-shaped configuration 5. A helical spring 3 secured at both ends to the diameter-reduced front end portion 2A of the core member 2 has an outer diameter of 0.355 mm. A coil line (helice) of the helical spring 3 is 0.072 mm in diameter. The core member 2 and the helical spring 3 are made of a stainless steel metal. The helical spring 3 and the core member 2 are spaced to form a non-integral zone L extending at least 20 mm from the leading end tip 4 of the diameter-reduced front end portion 2A. Consecutively from an end of the non-integral zone L, a series of doughnut-shaped securement points P are lengthwisely provided at regular spans 5 (10-30 mm) between an outer circumference of the diameter-reduced front end portion 2A and an inner circumference of the helical spring 3. The securement points P are made from a solder (e.g., gold alloy) to have approximately 1.0 mm in thickness.

The structure of the guide wire 1 is such that the guide wire 1 enables the manipulator to advance the front end portion 1A with a good steerability especially upon introducing the guide wire 1 through its leading elongation (approx. 120 mm) from the main aortic arch to the coronary artery of the cardiovascular system.

Dimensionally identical two guide wires are selected as shown in FIGS. 3, 4, the medical guide wire 1 is with the securement points P and the prior art guide wire 20 is without the securement points P. When the guide wires 1, 20 are bent generally into a U-shaped configuration with the same diameter, the guide wire 20 deforms with its radius of curvature R3, R4 successively reducing from the hand access portion to the front end portion of the medical guide wire due to the fact that the tapered-off core member changes its bending rigidity in the lengthwise direction. When the guide wire 20 changes its radius of curvature from R3 to R4, a point X of inflection appears at a boundary portion between the two radii of curvature R3, R4 in a manner to protract outward so as to form an irregular U-shaped configuration as a whole.

Although the guide wire 1 according to the invention deforms with its radius of curvature R1, R2 successively reducing due to the change of the bending rigidity of the tapered-off core member 2, a transit from the radius of curvature R1 to R2 is extremely smooth with no point X of inflection appeared at an interface portion between the two radii of curvature.

The reason why the transit from the radius of curvature R1 to R2 is extremely smooth is that a relative position between the core member 2 and the helical spring 3 becomes stable against a neutral plane of the core member 2 to provide the front end portion 1A with a stable moment of inertia in the lengthwise direction.

On the contrary, due to the clearance between the helical spring 23 and the core member 22, the guide wire 20 deforms the core member 22 to divert its central line from the neutral plane of the core member 22. This provides the front end portion 21A with a reduced moment of inertia so as to develop the point X of inflection.

The portion in which the point X of inflection is developed protracts significantly outward. The protracted portion is forced to push against an inner wall of the blood vessel to increase an insert resistance, potentially damaging the blood vessel and causing pain.

Since the guide wire 1 according to the invention develops no harmful point X of inflection, the guide wire 1 overcomes the problems of the prior art and significantly improves the recovery of the diseased area. The guide wire 1 also improves the steerability (rotation-following capability) upon inserting it into the somatic cavity. Namely, FIG. 5 shows a manner in which the guide wire 1 transmits the rotation of the front end portion 1A turned by 257 degrees in response to that of the hand access portion 2B manipulated by 360 degrees.

As opposed to the above case, the guide wire 20 transmits the rotation of the front end portion turned by 53 degrees in response to that of the hand access portion manipulated by 360 degrees. This shows that the rotation-following capability of the guide wire 1 is approximately five times as great as that of the guide wire 20.

The high rotation-following capability derived herein can be analyzed as follows:

When a torsional force is applied to both the ends of the helical spring, the torsional angle is generally in direct proportion to the winding number of the helical spring, and the rotational torque is substantially in inverse proportion to the winding number of the helical spring. With this theoretical analysis in mind, the guide wire 1 permits the securement points P to divide the helical spring 3 into a plurality of compartments, each of which is subjected to a unitary rotational torque to deform in accordance with the above proportional theory. It is true with the rotational torque. The rotational torque transmitted from the hand access portion 2B to the front end portion 1A in the guide wire 1 increases by 3-5 times as great as the rotational torque transmitted from the hand access portion to the front end portion in the guide wire 20.

Under the presence of the securement points P, the rotation-following capability and the rotational torque transmitted from the hand access portion 2B to the front end portion 1A are significantly improved to contribute to the stable remedial performance. The securement points P aligned at the predetermined spans S apparently differentiates the conventional idea to simply thicken the core member and the helical spring so as to build up their rigidity.

Since it is possible to dimensionally adjust the spans S differently between the securement points P, a shorter span enables the front end portion 1A to a greater rigidity while a longer span enables the front end portion 1A to a smaller rigidity. This adjustment can quantitatively provide the front end portion 1A with an appropriate bending rigidity by anticipating a critical radius of curvature ensured to the front end portion 1A based on an ordinary extent of the pushing force which the hand access portion 2B exercises.

The adjustment of the bending rigidity makes it possible to render an abnormal resistance detectable to the hand access portion 2B upon inserting the front end portion 1A into the bifurcated or sharply curved bight portion of the blood vessel in which the guide wire 1 is likely subjected to an abnormal deformation. In this situation, the manipulator feels the abnormal resistance and rotational resistance due to the abnormal bending deformation, and can ease the operational force within an allowable limit. This protects the front end portion 1A of the guide wire 1 against the damage, while at the same time, avoiding inadvertent damage to the inner wall of the blood vessel. This makes it possible to advance the front end portion 1A smoothly into the blood vessel with an ordinary amount of the manipulation force. These arrangements enable manufacturers to produce diversified guide wires of minimum allowable radii of curvature compatible to the conditions and the diseased area of the blood vessel, and thus significantly contributing to improvement of the remedial performance.

FIGS. 6 through 7 show a second embodiment of the invention in which the securement points P are aligned at irregular spans S. The spans S decrease progressively in an arithmetic or geometric series as exemplified by S1, S2, . . . , SN from the hand access portion 2B to the leading end tip 4 as shown in FIG. 6. Alternatively, the spans S decrease progressively in the arithmetic or geometric series as exemplified by S1, S2, . . . , SN from the leading end tip 4 to the hand access portion 2B as shown in FIG. 7.

The adjustment of the spans S makes it possible to dimensionally determine the bending rigidity of the front end portion 1A of the guide wire 1 as desired. The magnitude of the bending rigidity determines the radius of curvature of the front end portion 1A bendable in each of the spans S. This enables the front end portion 1A to smoothly bend with the radius of curvature corresponding to the tortuous and meandering blood vessel (e.g., cardiovascular system) upon inserting the front end portion 1A into the blood vessel.

The progressively changing spans S determine the combined performance of the core member 2 and the helical spring 3 which deform and torsionally move in cooperation with each other, while at the same time, determining the desired radius of curvature and the rotational torque of the front end portion 1A bendable in each of the spans S. The securement points P may be placed at irregular intervals (e.g., at random) to produce the spans S of different widths. The spans S of equal width and the spans S arranged in the arithmetic or geometric series may be combined as necessary.

In a modified form, the securement points P are made of a radiopaque material to provide the guide wire 1 with a measurement function. With the use of the radiation rays, it is possible to measure a dimensional size of the diseased area from dimensions of the spans S and the diameter of the securement points P while monitoring an image upon inserting the guide wire 1 into the somatic cavity.

FIG. 8 shows a third embodiment of the invention in which the helical spring 3 is made of two different metals. One is a platinum wire and the other a stainless steel wire. The platinum and stainless steel wires are connected in series by a welding procedure, and withdrawn to form a single raw wire until the coil line becomes 0.072 mm in diameter. The single raw wire is wound around a mandrel (not shown) to form a radiopaque helical configuration of different metals as a whole. Namely, the helical spring 3A is the radiopaque helical spring 3A and the radiotransparent helical spring 3B in turn located from a front end portion to a rear end portion of the helical spring 3 so as to provide a unitary helical configuration of different metals. An entire length (CL:30 mm) of the radiopaque helical spring 3A is an integral multiple of the span S (10 mm) formed by the securement points P aligned with the radiotransparent helical spring 3B at regular intervals.

In this instance, a breadth of the non-integral zone L is 25 mm in order to stabilize the welded portion between the two helical springs 3A, 3B. Lengths L2 and L3 are in turn determined to be 50 mm and 90 mm by way of example.

With the use of the X-rays, it is possible to measure a dimensional size of a diameter of the blood vessel at an injection of the contrast medium, while at the same time, measuring sizes of the diseased area and peripheral sections in the neighborhood of the diseased area based on the dimensional length and diameter of the radiopaque helical spring 3A and the securement points P based on the monitored image observed upon inserting the guide wire 1 into the somatic cavity.

Considering that the length of the radiopaque helical spring 3A is an integer multiple of the span S, it is possible to precisely measure the blood vessel complicatedly curved and perspectively projected on the planar image monitor by comparing the entire length of the radiopaque helical spring 3A with the spans S of the securement points P observed from the monitored image. Upon forming the securement points P, the radiopaque ball made of a gold, silver or tungsten solder is heated to melt into the doughnut-shaped configuration (approx. 0.3-1.0 mm in thickness) to concentrically connect the helical spring 3 to the care member 2 in one piece.

Due to the radiotransparent helical spring 3B made of the stainless steel metal, there arises a spring back difference between the two helical springs 3A and 3B. The spring back of the helical spring 3B suppresses that of helical spring 3A so that the difference of the spring back between the two springs 3A, 3B works to diametrically reduce the radiopaque helical spring 3A in a fashion tapered off toward the leading end tip 4 of the core member 2. In this situation, the helical spring 3A is highly tapered off more than a case in which whole the helical spring 3 is diametrically reduced progressively in the lengthwise direction. This helps the helical spring 3A advance smoothly into the vascular stenosis area, the intima and the adventitial coat upon inserting the guide wire 1 into the blood vessel.

Figure 9:
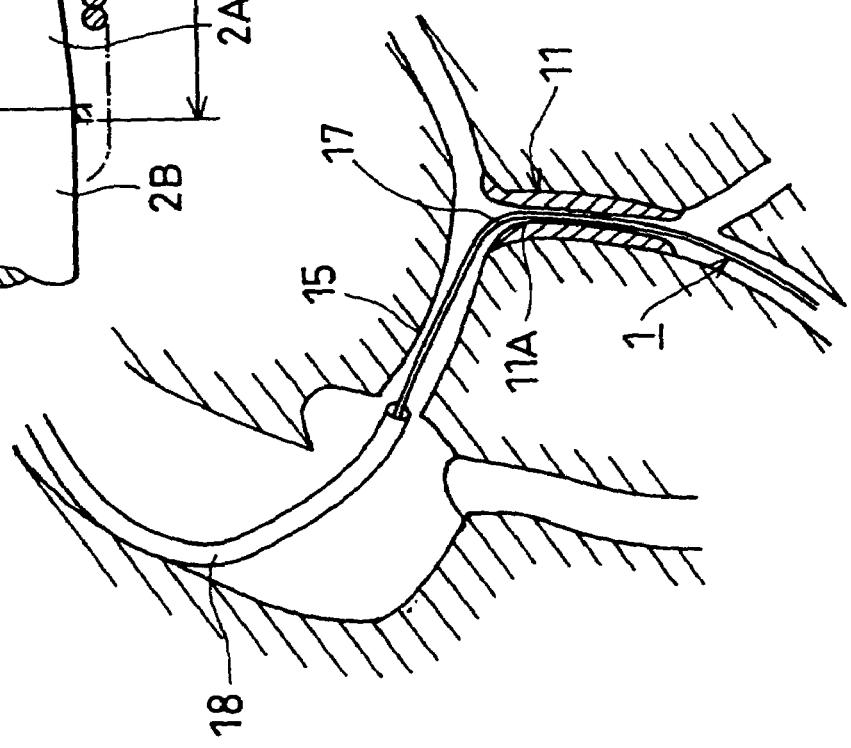
FIG. 9 is an explanatory view showing how the medical guide wire works.

With the conventional art in mind, upon treating the coronary artery disease, the guide wire is inserted into the coronary artery by 100-120 mm. The disease likely develops at the bifurcated portion of the blood vessel. By way of illustration, the vascular stenosis area 11 likely develops at a portion 16 advanced by 30-60 mm from an entrance of the left coronary artery 15 as shown in FIG. 9. Upon measuring the vascular stenosis area 11 by using an elongation extended by approx. 50 mm from a leading end of the guide wire as disclosed by Japanese Domestic Laid-open Patent Application No. 7-500749, an insertable length of the guide wire is only by 30-60 mm from the entrance of the left coronary artery 15. At this time, the blood streams cause a pliable leading end of the guide wire to oscillate sufficiently to hinder precise measurements against the diseased area.

With the radiopaque helical spring 3A diametrically reduced progressively, the guide wire 1 enables the manipulator to advance the helical spring 3 deep beyond the vascular stenosis area 11. With the securement points P placed at regular intervals to extend by 140 mm from the leading end tip 4, the guide wire 1 enables the manipulator to move the helical spring 3 until the last securement point P (17) meets an entrance 11A of the vascular stenosis area 11. This makes it possible to advance the guide wire 1 stably through a catheter 18 deep into the vascular stenosis area 11 without oscillation of the pliable helical spring 3 against the blood streams, thus enabling the manipulator to readily measure the diseased area with a high precision.

When the helical spring 3 is limited to the structure in which the helical spring 3 is formed by winding a single wire around a mandrel (not shown) to provide a single wound spring configuration as a fourth embodiment of the invention, the following advantages are obtained.

Figure 10:
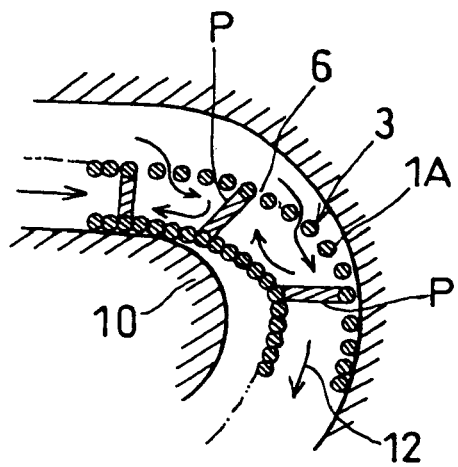
FIG. 10 is an explanatory view showing how a medical guide wire works according to a fourth embodiment of the invention.

Namely, upon advancing the front end portion 1A of the guide wire 1 into a meandering portion 10 of the blood vessel as shown in FIG. 10, the guide wire 1 bends the front end portion 1A to render a gap 6 wider between neighboring coil lines at a tensile side of the front end portion 1A. Under the presence of the front end portion 1A and the meandering blood vessel, the blood stream increases its velocity to run into a helical spring 3 through the gap 6 so as to exert a liquid pressure against the securement points P to provide it with a forward propelling force 12. The forward propelling force 12 is multiplied by the number of the securement points P to enable the manipulator to advance the front end portion 1A deeper into the tortuous blood vessel. The front end 2A of the core member 2 is tapered off so that the forward propelling force 12 against the securement points P increases progressively as approaching the front end portion 1A of the guide wire 1. This is because the securement points P increase its pressure area successively as approaching the front end portion 1A of the guide wire 1. This theory effectively assists the front end portion 1A to advance into the blood vessel through its entrance where an insertion resistance is likely to increase.

In a wire-strand structure in which a plurality of metallic wires are stranded to form a tubular body, upon bending the front end portion, coil lines of the helical spring relatively slide at its tensile side and no gap appears between the neighboring coil lines of the helical spring. There develops no propelling force in the forward direction due to the absence of the blood streams running inside the helical spring, thus making it difficult to advance the front end portion deep into the tortuous blood vessel. It is true with the case in which the securement points P are not provided.

Figure 12:
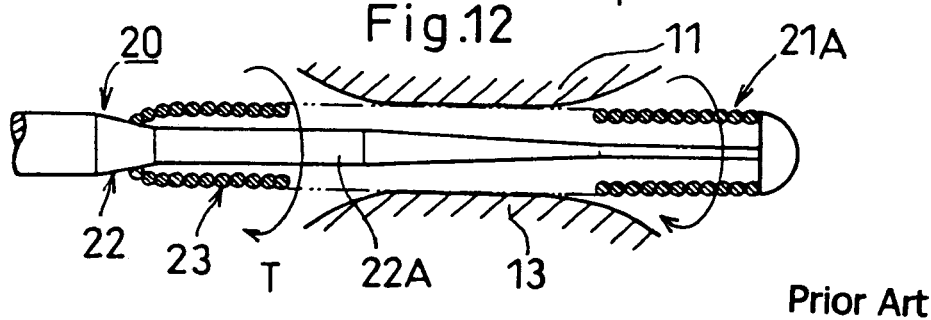
FIG. 12 is a longitudinal cross sectional view of a prior art medical guide wire with the medical guide wire inserted into the vascular stenosis area.

In the art guide wire 20 which has no means corresponding to the securement points P as shown in FIG. 12, the front end portion 21A is stuck at a middle portion 13 of the vascular stenosis area 11 upon inserting the front end portion 21A of the helical spring 23 into the vascular stenosis area 11. In order to transmit the rotational torque T to the front end portion 21A beyond the middle portion 13, it is necessary to exercise a torsional angle in direct proportion to the winding number of the front end portion 21A beyond the middle portion 13. This requires a greater rotational force which would inadvertently deform or damage the core member 22 and helical spring 23.

Figure 11:
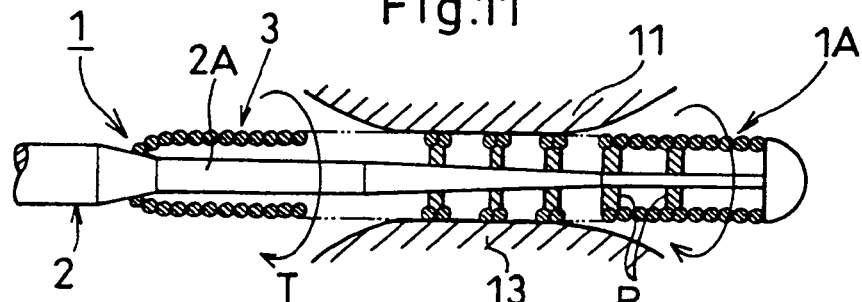
FIG. 11 is a longitudinal cross sectional view of the medical guide wire with the medical guide wire inserted into a vascular stenosis area.

Under the presence of the securement points P as shown in FIG. 11, it is possible to transmit the rotational torque T to the front end portion 1A beyond the middle portion 13 with a smaller rotational force needed to rotate the winding number of a single one span S. This enables the manipulator to readily rotate the guide wire 1, while at the same time, protecting the core member 2 and helical spring 3 against damage and unintentional deformation.

The torsional rigidity between the securement points P is in direct proportion to the winding number of the span S, and is in inverse proportion to a diameter raised to 4th power concerning to the front end 2A of the core member 2.

Figure 13:
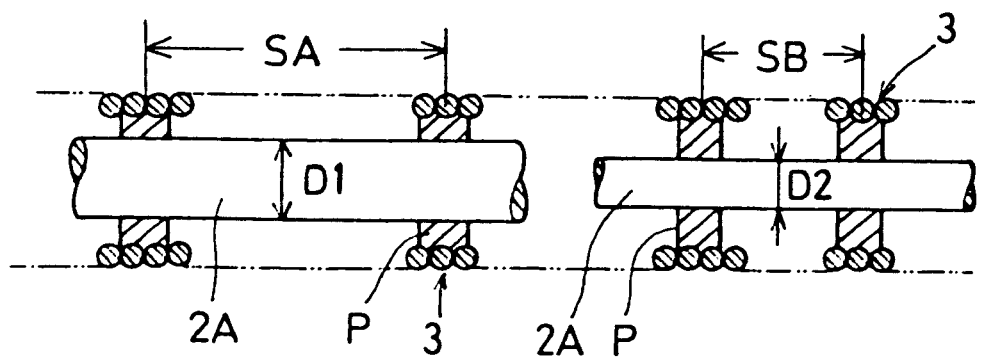
FIG. 13 is an explanatory view showing how the medical guide wire works.

In order to diametrically reduce the front end 2A of the core member 2 favorably tapered off progressively as approaching the leading end tip 4, a numerical relationship $SB/SA \leqq = (D2/D1)^4$ is required between the span SA and a greater diameter D1 at the diameter-increased portion of the core member 2, and the span SB and a smaller diameter D2 at the diameter-reduced portion of the core member 2 as shown in FIG. 13.

It is to be noted that the securement points P are not confined to the doughnut-shaped configuration but any shape will do only if the securement points P can integrally connect the helical spring 3 concentrically or eccentrically to the core member 2. The helical spring 3 may be in the form of a wire-stranded hollow configuration. The helical spring 3 may have a gap between the neighboring coil lines of the helical spring 3.

What is claimed is:

1. A medical guide wire in which a flexible elongated core member has a diameter-reduced front end portion and a hand access portion diametrically greater than said diameter-reduced front end portion, and a helical spring secured at both ends to said diameter-reduced front end portion;

said helical spring being a radiopaque helical spring and a radiotransparent helical spring in turn arranged from a front end portion to a rear end portion of said helical spring so that said helical spring provides a unitary single helical configuration of different metal wires;

said diameter-reduced front end portion being at least one of diametrically decreased progressively toward a front end of said diameter-reduced front end portion or tapered-off toward said front end of said diameter-reduced front end portion;

said helical spring and said core member being spaced to form a non-integral zone extending at least 20 mm from said front end of said diameter-reduced front end portion;

an inner circumference of said helical spring and an outer circumference of said core member being secured to form a plurality of securement points aligned in a lengthwise direction of said core member at regular interval spans arranged from said non-integral zone to a rear end of said helical spring, said securement points being formed from a radiopaque metal; and said spans of said securement points being located within a range of 50 mm to 140 mm from said front end of said diameter-reduced front end portion; and a length of said radiopaque helical spring being equal to an integral multiple of a span between neighboring ones of said securement points aligned within the radiotransparent helical spring.

2. The medical guide wire according to claim 1, wherein said regular interval spans of said securement points are determined to be 10 mm.

3. The medical guide wire according to claim 2, in which a dimension SA is defined as the distance between securement points at a diameter-increased portion of said core member, a dimension SB is defined as the distance between said securement points at said diameter-reduced portion of said core member, a dimension D1 is defined as the diameter of said diameter-increased portion of said core member, and a dimension D2 is defined as the diameter of said diameter-reduced portion of said core member; and wherein a relationship of $(SB/SA) \leqq (D2/D1)^4$ exists.

4. The medical guide wire according to claim 1, wherein said securement points are aligned with 10 mm as regular interval spans, and said length of said radiopaque helical spring measuring 30 mm.

5. The medical guide according to claim 1, including a plurality of securement points aligned at irregular intervals in the lengthwise direction of said core member.

6. The medical guide wire according to claim 1, in which a dimension SA is defined as the distance between securement points at a diameter-increased portion of said core member, a dimension SB is defined as the distance between said securement points at said diameter-reduced portion of said core member, a dimension D1 is defined as the diameter of said diameter-increased portion of said core member, and a dimension D2 is defined as the diameter of said diameter-reduced portion of said core member; and wherein a relationship of $(SB/SA) \leqq (D2/D1)^4$ exists.

7. The medical guide wire according to claim 1, wherein said securement points connect said helical spring to said core member in one piece, and having a thickness ranging from approximately 0.3 mm to 1.0 mm.

8. A medical guide wire in which a flexible elongated core member has a diameter-reduced front end portion and a hand access portion diametrically greater than said diameter-reduced front end portion and a helical spring secured at both ends to said diameter-reduced front end portion;

said diameter-reduced front end portion being at least one of diametrically decreased progressively toward a front end of said diameter-reduced front end portion or tapered-off toward said front-end of said diameter-reduced front end portion said helical spring being a radiopaque helical spring and a radiotransparent helical spring in turn arranged from a front end portion to a rear end portion of said helical spring;

said helical spring and said core member being spaced to form a non-integral zone extending at least 20 mm from said front end of said diameter reduced front end portion;

an inner circumference of said helical spring and an outer circumference of said core member being secured to form a plurality of securement points aligned in a lengthwise direction of said core member at certain spans arranged from said non-integral zone to a rear end of said helical spring;

said spans of said securement points being located within a range of 50 mm-140 mm from said front end of said diameter-reduced front end portion; and a dimension SA being defined as the distance between securement points at a diameter increased portion of said core member a dimension SB defined as the distance between said securement points at said diameter-reduced portion of said core member, a dimension D1 defined as the diameter of said diameter-increased portion of said core member, and a dimension D2 defined as the diameter of said diameter-reduced portion of said core member, wherein a relationship of $(SB/SA) \leqq (D2/D1)^4$ exists.

* * * * *